(12) United States Patent
Masaoka et al.

(10) Patent No.: US 9,381,504 B2
(45) Date of Patent: Jul. 5, 2016

(54) DEODORIZING MATERIAL, PROCESS FOR MANUFACTURING DEODORIZING MATERIAL, AND DEODORIZING DEVICE

(71) Applicants: Hiroshima University, Higashi-Hiroshima-shi, Hiroshima (JP); Yokota Trading Co., Ltd., Naku-ku, Hiroshima-shi (JP)

(72) Inventors: Yoshikuni Masaoka, Higashi-Hiroshima (JP); Masatake Tagawa, Naka-ku (JP); Toshihiko Ohara, Minami-ku (JP)

(73) Assignees: HIROSHIMA UNIVERSITY, Naka-Ku, Hiroshima-Shi, Hiroshima (JP); YOKOTA TRADING CO., LTD., Naka-Ku, Hiroshima-Shi, Hiroshima (JP)

( * ) Notice: Subject to any disclaimer, the term of this patent is extended or adjusted under 35 U.S.C. 154(b) by 0 days.

(21) Appl. No.: 14/417,096

(22) PCT Filed: Jul. 17, 2013

(86) PCT No.: PCT/JP2013/069423
§ 371 (c)(1),
(2) Date: Jan. 23, 2015

(87) PCT Pub. No.: WO2014/024650
PCT Pub. Date: Feb. 13, 2014

(65) Prior Publication Data
US 2015/0202608 A1     Jul. 23, 2015

(30) Foreign Application Priority Data
Aug. 10, 2012 (JP) ................................ 2012-178967

(51) Int. Cl.
*B01J 31/06* (2006.01)
*C09B 11/24* (2006.01)
(Continued)

(52) U.S. Cl.
CPC .. *B01J 31/06* (2013.01); *A61L 9/01* (2013.01); *A61L 9/18* (2013.01); *B01D 53/38* (2013.01);
(Continued)

(58) Field of Classification Search
None
See application file for complete search history.

(56) References Cited

U.S. PATENT DOCUMENTS 3,885,961 A * 5/1975 Kimura .................. G03G 5/087
430/96
3,925,076 A * 12/1975 Heimsch .................. G03C 1/73
101/129

(Continued)

FOREIGN PATENT DOCUMENTS

| JP | 2004-350935 A | 12/2004 |
| JP | 2006-212383 A | 8/2006 |
| JP | 2008-284272 A | 11/2008 |

OTHER PUBLICATIONS

Extended European Search Report dated Mar. 3, 2016 for Application No. EP 13 82 7749.

(Continued)

*Primary Examiner* — Melvin C Mayes
*Assistant Examiner* — Colette Nguyen
(74) *Attorney, Agent, or Firm* — Howard & Howard Attorneys PLLC

(57) ABSTRACT

A deodorizing material is a cured substance that is obtained by dissolving a photosensitizing colorant in an unsaturated polyester resin composition which contains unsaturated polyester and a monomer copolymerizable with the unsaturated polyester and which is in a liquid state at a room temperature, and by adding a curing agent to let the liquid cured. This deodorizing material changes from the base state to the singlet excitation state, and further to the triplet excitation state upon irradiation with light in a gas phase containing oxygen and odor components. This energy is given to the oxygen molecules to produce singlet oxygen. The oxidation action of the produced singlet oxygen decomposes the odor components.

12 Claims, 5 Drawing Sheets

(51) Int. Cl.
    *A61L 9/18*     (2006.01)
    *B01J 35/00*     (2006.01)
    *A61L 9/01*     (2006.01)
    *B01D 53/86*     (2006.01)
    *B01J 31/02*     (2006.01)
    *C08L 67/06*     (2006.01)
    *B01J 37/34*     (2006.01)
    *B01J 37/00*     (2006.01)
    *C09B 67/42*     (2006.01)
    *C09B 67/02*     (2006.01)
    *B01D 53/38*     (2006.01)
    *A61L 9/20*     (2006.01)
    *B01J 35/08*     (2006.01)
    *B01J 35/02*     (2006.01)

(52) U.S. Cl.
    CPC ........ *B01D 53/8603* (2013.01); *B01D 53/8606* (2013.01); *B01D 53/8678* (2013.01); *B01J 31/0202* (2013.01); *B01J 31/0208* (2013.01); *B01J 31/0232* (2013.01); *B01J 35/004* (2013.01); *B01J 37/0009* (2013.01); *B01J 37/344* (2013.01); *C08L 67/06* (2013.01); *C09B 11/24* (2013.01); *C09B 67/0092* (2013.01); *C09B 67/0097* (2013.01); *A61L 9/205* (2013.01); *A61L 2209/12* (2013.01); *A61L 2209/21* (2013.01); *B01D 2251/102* (2013.01); *B01D 2255/70* (2013.01); *B01D 2255/802* (2013.01); *B01D 2257/306* (2013.01); *B01J 35/02* (2013.01); *B01J 35/08* (2013.01); *B01J 2231/005* (2013.01); *B01J 2231/70* (2013.01); *B01J 2531/002* (2013.01); *C08L 2666/70* (2013.01)

(56) References Cited

U.S. PATENT DOCUMENTS

| | | | |
|---|---|---|---|
| 2007/0090153 A1* | 4/2007 | Naito | A61K 8/19 228/101 |
| 2010/0158840 A1* | 6/2010 | Hiramoto | A61K 8/19 424/65 |
| 2011/0023720 A1 | 2/2011 | Chen | |
| 2013/0136713 A1* | 5/2013 | Terada | A61L 9/01 424/76.1 |

OTHER PUBLICATIONS

International Search Report (PCT/JP2013/069423); Date of Mailing: Sep. 10, 2013.
Written Opinion (PCT/JP2013/069423); Date of Mailing: Sep. 10, 2013.

* cited by examiner

DEODORIZING MATERIAL, PROCESS FOR MANUFACTURING DEODORIZING MATERIAL, AND DEODORIZING DEVICE

CROSS REFERENCE TO RELATED APPLICATION

This application is a national phase application of PCT/JP2013/069423, filed Jul. 17, 2013, which claims priority to Japanese Patent Application No. 2012-178967, filed Aug. 10, 2012, the disclosures of which are hereby incorporated by reference in their entirety.

TECHNICAL FIELD

The present disclosure relates to a deodorizing material, a producing method of the deodorizing material, and a deodorizing device.

BACKGROUND ART

A technology of decomposing odor components using photosensitizing colorants is already known. For example, Patent Literatures 1, 2 disclose devices that blow air to a liquid containing photosensitizing colorants like rose bengal to decompose odor components (see Patent Literatures 1, 2).

In addition, Patent Literature 3 discloses a technology of decomposing odor components by immobilizing photosensitizing colorants on a carrier, emitting light thereto in a gas phase containing oxygen to produce singlet oxygen, and causing the singlet oxygen to contact the odor components in the gas phase. Example carriers to immobilize the photosensitizing colorants are a polyamide resin, and a polyester resin.

Still further, Patent Literature 4 discloses a singlet oxygen producing film utilizing photosensitizing colorants. This singlet oxygen producing film is obtained through a process of causing photosensitizing colorants formed of water-soluble organic compounds to be electrostatically adsorbed by a carrier that can be electrostatically coupled with the photosensitizing colorants to obtain composite particles, a process of dispersing the composite particles in an aqueous medium to obtain a dispersion liquid, and a process s of suctioning and filtrating the dispersion liquid with a membrane filter including the outermost layer formed with holes that have a smaller diameter than the particle diameter of the composite particle, thereby causing the composite particles to stick on the one surface of the membrane filter as a film.

CITATION LIST

Patent Literature

Patent Literature 1: Unexamined Japanese Patent Application Kokai Publication No. 2008-284272.
Patent Literature 2: Unexamined Japanese Patent Application Kokai Publication No. 2010-57908.
Patent Literature 3: Unexamined Japanese Patent Application Kokai Publication No. 2006-212383.
Patent Literature 4: Unexamined Japanese Patent Application Kokai Publication No. 2012-87025.

SUMMARY OF INVENTION

Technical Problem

According to Patent Literatures 1, 2, gas is blown to the odor liquid in which the photosensitizing colorants are dissolved. When the gas is blown to the odor liquid, since the resistance is large, a circulation device like a large-scale pump that can circulate the gas through the odor liquid is necessary. Hence, the deodorizing device becomes large in size with a less general versatility.

According to Patent Literature 3, since the material having the colorants stuck and carried on the surface of the carrier, such as a polyester resin or a polyamide resin, the colorants are detached from the carrier, and this technology is not suitable for a long-term use. In addition, the photosensitizing colorants stuck on the carrier like a resin attenuate light emitted from a light source. Hence, light does not easily reach the photosensitizing colorants stuck on the carrier that does not directly face the light source. Accordingly, the production amount of singlet oxygen that contributes to the decomposition of odor components is little.

According to the singlet oxygen producing film of Patent Literature 4, it is necessary to put such a film in a special deodorizing device or the like adopted for the film, and it is difficult to apply this film to various deodorizing devices. Hence, the general versatility is not high. Moreover, the singlet oxygen producing film is obtained through multiple processes, thus cannot obtained easily.

The present disclosure has been made in view of the aforementioned circumstances, and it is an objective of the present disclosure to provide a deodorizing material, a producing method of the deodorizing material, and a deodorizing device which have a high general versatility, and which have an excellent decomposition performance of odor components.

Solution to Problem

A deodorizing material according to a first aspect of the present disclosure includes a cured substance that is obtained by dissolving a photosensitizing colorant in an unsaturated polyester resin composition which contains unsaturated polyester and a monomer copolymerizable with the unsaturated polyester and which is in a liquid state at a room temperature, and by adding a curing agent to let the liquid cured, in which the photosensitizing colorant is excited upon irradiation with light in a gas phase containing oxygen and an odor component, gives energy to the oxygen to produce singlet oxygen, thereby decomposing the odor component.

It is preferable that the photosensitizing colorant should be rose bengal.

It is preferable that the applied curing agent should have a heat generation temperature of equal to or lower than 100° C. at a time of curing.

It is preferable that the photosensitizing colorant of equal to or greater than 1.5 g but smaller than 3.0 g should be dissolved in the unsaturated polyester resin composition of 100 ml.

A deodorizing material producing method according to a second aspect of the present disclosure includes: dissolving a photosensitizing colorant in an unsaturated polyester resin composition which contains unsaturated polyester and a monomer copolymerizable with the unsaturated polyester, and which is in a liquid state at a room temperature; and adding a curing agent to let the liquid cured.

It is preferable that the applied photosensitizing colorant should be rose bengal.

It is preferable that the applied curing agent should have a heat generation temperature of equal to or lower than 100° C. at a time of curing.

It is preferable that the photosensitizing colorant of equal to or greater than 1.5 g but smaller than 3.0 g should be dissolved in the unsaturated polyester resin composition of 100 ml.

A deodorizing device according to a third aspect of the present disclosure includes: a container in which the deodorizing material according to any one of Claims 1 to 4 is filled; an inlet that guides air containing an odor component into the container; and an outlet that discharges the air from the container.

It is preferable that the deodorizing device should further include an air circulation device that causes, through the inlet and the outlet, the air to be in contact with each deodorizing material filled in the container.

It is preferable that the deodorizing device should further include a light emitting device that emits light to the deodorizing material.

Advantageous Effects of Invention

The deodorizing material of the present disclosure is a cured substance obtained by dissolving the photosensitizing colorants in the unsaturated polyester resin composition which contains unsaturated polyester and a monomer that can be copolymerized with the unsaturated polyester, and which is in a liquid state at a room temperature, and by adding the curing agent to let the liquid cured. Since it is a solid body that can be formed in a desired size, the handling of the deodorizing material is easy and the deodorizing material can be built in various deodorizing devices. Hence, the general versatility is excellent.

In addition, since the deodorizing material is light transmissive, emitted light passes through the deodorizing material, and can reach other deodorizing materials that do not directly face with a light source. Hence, the photosensitizing colorants in the deodorizing materials not directly facing with the light source are also excited. Singlet oxygen can be efficiently produced by the deodorizing materials filled in or built in the deodorizing device or the like, resulting in an excellent decomposition performance of odor components.

DESCRIPTION OF EMBODIMENTS (Deodorizing Material)

Figure 1:
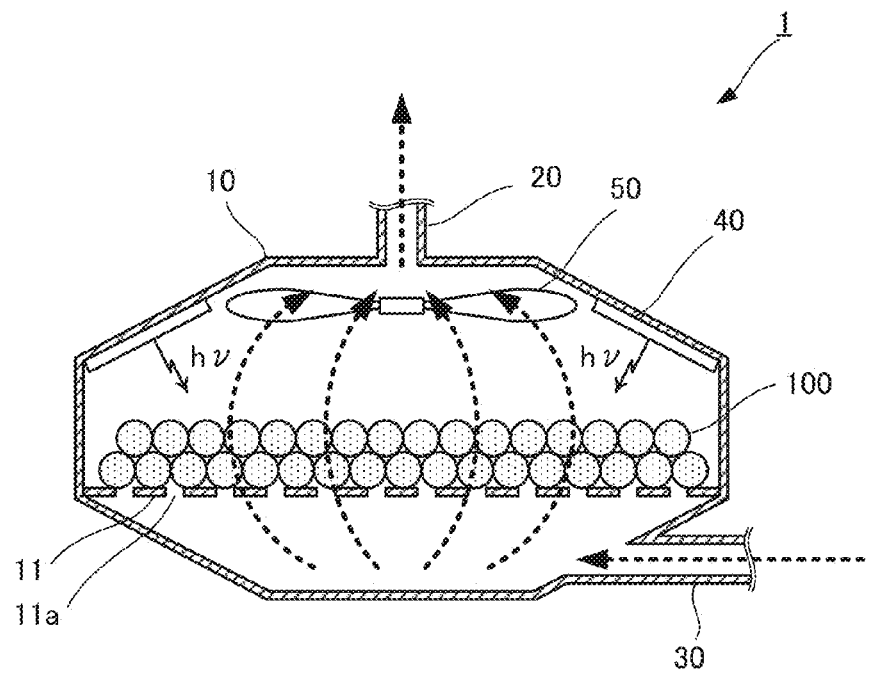
FIG. 1 is a schematic structural diagram illustrating a first example deodorizing device.

A deodorizing material according to an embodiment is a cured substance that is obtained by dissolving photosensitizing colorants in an unsaturated polyester resin composition which contains unsaturated polyester and a monomer that can be copolymerized with unsaturated polyester, and which is in a liquid state at a room temperature, and by adding a curing agent thereto to let the liquid cured. The deodorizing material has the photosensitizing colorants dissolved in the unsaturated polyester resin. Although the deodorizing material is colored by the photosensitizing colorants, the deodorizing material is transparent with a color, and is light transmissive. It is preferable that the light transmissivity should be equal to or higher than 5% when measured for a deodorizing material that has a thickness of 2 mm.

As will be discussed later, the deodorizing material decomposes odor components contained in air. When irradiated with light, the photosensitizing colorants in the deodorizing material change from the base state to the singlet excitation state, and further to the triplet excitation state. In this case, when the deodorizing material is present in air that contains oxygen and odor components, the photosensitizing colorants in the triplet excitation state give the energy thereof to the oxygen molecules in the base state, thereby producing singlet oxygen. The produced singlet oxygen is a kind of active oxygen, and is an extremely unstable substance but has a remarkable oxidation action. The oxidation action of the singlet oxygen decomposes the odor components.

In addition, the singlet oxygen has an action of decomposing germs, and thus germs in air can be sterilized.

Example odor components that can be decomposed are mercaptan, methyl sulfide, dimethyl sulfide, and hydrogen sulfide.

The above-explained deodorizing material can be obtained as follow. Photosensitizing colorants are added to an unsaturated polyester resin composition to dissolve the photosensitizing colorants therein. The photosensitizing colorants like rose bengal has an excellent compatibility with the unsaturated polyester resin composition, thus can be easily dissolved therein. Next, a curing agent is added, and the resin composition is poured in a predetermined mold form or the like. After a predetermined time has elapsed, the unsaturated polyester and the monomer are copolymerized and cured, and thus the deodorizing material can be obtained.

An example unsaturated polyester is normal unsaturated polyester in a liquid state at a normal temperature. Unsaturated polyester can be obtained from α,β-unsaturated dibasic acid, saturated dibasic acid, and multiple alcohol. An example α,β-unsaturated dibasic acid is anhydrous maleic acid, maleic acid, fumaric acid, mesaconic acid, tetracosaanoic acid, itaconic acid or alkyl-ester group thereof. An example saturated dibasic acid is anhydrous phthalic acid, orthophthalic acid, isophthalic acid, terephthalic acid, tetrahydrophthal acid, halogenated anhydrous phthalic acid, adipic acid, succinic acid, sebasic acid, or alkyl-ester group thereof. An example multiple alcohol is ethylene glycol, diethyl glycol, propylene glycol, dipropylene glycol, butylene glycol, neopentyl glycol, hexylene glycol, bisphenol hydride A, 2,2'-di(4-hydroxylpropoxyphenil)propane, 2,2'-di(4-hydroxylethoxyphenil) propane, ethylene oxide, or propylene oxide. The above-explained unsaturated polyester does not have a particular polymerization degree as long as the unsaturated polyester has unsaturated radical like double bond in the molecules, is obtained by a polymerization through ester bonding, is in a liquid state at a room temperature when mixed with a monomer that can be copolymerized therewith, and becomes a high molecular mass state and cured by a curing agent to be discussed later.

An example monomer that can be copolymerized with unsaturated polyester is alkenyl aromatic monomer, such as styrene, α-methyl styrene or t-butyl styrene, alkyl ester, such as acrylic acid or methacrylic acid, or vinyl acetate, but styrene is especially preferable among those.

In addition, the unsaturated polyester resin composition may further contain, in addition to the above-mentioned substances, a low contractile agent, a filler, a thickening agent, a demolding agent, a polymerization inhibitor, and the like.

As the unsaturated polyester resin composition, a commercially available unsaturated polyester resin composition with a high transparency, for example, a clear polyester resin (product number: F-04 made by EPOCH Corporation) is applicable.

An example curing agent is an organic peroxide which starts a radical reaction, and which causes a copolymerization of unsaturated polyester with a monomer. Example organic peroxides are ethyl-methyl-ketone-peroxide, dicumyl-peroxide, t-butyl-hydro-peroxide, cumene-hydro-peroxide, lauroyl-peroxide, cumene-peroxide, benzoyl-peroxide, t-butyl-isopropyl-peroxy-carbonate, 1,1-dibutyl-peroxy-3,3,5-trimethyl-cyclo-hexanone, t-butyl-peroxy-2-ethyl-hexanoate, amyl-peroxy-2-ethyl-hexanonate, 2-ethyl-hexyl-peroxy-2-ethyl-hexanoate, t-butyl-peroxy-benzoate, and t-hexyl-peroxy-benzoate, and among those substances, methyl-ethyl-ketone-peroxide is preferable. It is preferable that the curing agent should be a low-heat-generation type which has a low heat generation temperature at the time of curing, and the curing agent that has a heat generation temperature of equal to or lower than 100° C. at the time of curing is preferable. When the heat generation temperature at the time of curing is high, the photosensitizing colorants may be carbonated (brownish discoloration phenomenon), the structure of the photosensitizing colorants may be changed, and thus the deodorization performance may be lost. In addition, when the heat generation temperature at the time of curing is high, cracks or shrinkages may occur, decreasing the light transmissivity of the deodorizing material to be obtained.

As the curing agent, a commercially available curing agent for unsaturated polyester resin compositions, for example, PERCURE-HB (compositions: ethyl-methyl-ketone-peroxide and dimethyl phthalate) (maximum heat generation temperature: 49° C.) (product name, made by NOF Corporation) is applicable.

When irradiated with light, the photosensitizing colorants change from the base state to the singlet excitation state, and further to the triplet excitation state. In this case, when the photosensitizing colorants are present in air that contains oxygen and odor components, the photosensitizing colorants in the triplet excitation state give the energy thereof to the oxygen molecules in the base state, thereby producing singlet oxygen. The produced singlet oxygen decomposes the odor components through an oxidation action. Example photosensitizing colorants are, in addition to rose bengal, fullerene, and methylene blue. One of or equal to or greater than two kinds of those substances may be contained. Rose bengal is a colorant that is utilized for foods, and has a high safeness. Hence, application of rose bengal is suitable.

The obtained deodorizing material can be directly applied, or may be crushed in a predetermined shape with a predetermined size. The shape of the deodorizing material is not limited to any particular one, such as a cubic shape (for example, a length of a side is 1 mm to 50 mm), a spherical shape (for example, a diameter of 1 mm to 50 mm), a bar shape (for example, a diameter of 1 mm to 10 mm, and a length of 10 mm to 1000 mm), and a tabular shape (for example, a thickness of 1 mm to 10 mm, and a length of 5 mm to 1000 mm). In addition, the size of the deodorizing material is not limited to any particular one, and can be an appropriate size in accordance with the application. The smaller the deodorizing material is, the more the total surface area of the deodorizing material increases, and the larger the contact area between air and the deodorizing material becomes. Hence, the resistance increases, disturbing the circulation of air. Conversely, the larger the deodorizing material is, the more the total surface area of the deodorizing material filled in a container or the like decreases, and the smaller the contact area between air and the deodorizing material becomes. Hence, air can be easily circulated. Accordingly, the size of the deodorizing material can be selected as needed such that when an air circulation device that has high suction performance and wind blowing performance, the deodorizing material with a small size is applied, and when an air circulation device that has not so high suction performance and wind blowing performance, the deodorizing material with a large size is applied.

A preferable component rate between unsaturated polyester and the monomer in the unsaturated polyester resin composition is, 30 to 80 wt % for unsaturated polyester, and 70 to 20 wt % for the monomer. When unsaturated polyester is less than 30 wt % and the monomer exceeds 70 wt %, the mechanical properties of the deodorizing material to be obtained as a cured substance tend to decrease. Conversely, when unsaturated polyester exceeds 80 wt %, and the monomer is less than 20 wt %, the viscosity of the unsaturated polyester resin composition becomes high, resulting in a difficulty in application.

A preferable blending ratio between the unsaturated polyester resin composition and the photosensitizing colorants is, relative to 100 ml of the unsaturated polyester resin composition, equal to or greater than 1.5 g and less than 3.0 g of the photosensitizing colorants, and preferably, 1.7 g to 2.8 g, more preferably, 1.8 g to 2.5 g, and most preferably, 1.8 g to 2.3 g. When the blending ratio of the photosensitizing colorants is small, the amount of photosensitizing colorants in the deodorizing material to be obtained becomes little, and thus the amount of singlet oxygen to be produced becomes little. Conversely, when the blending ratio of the photosensitizing colorants is high, the light transmissivity of the deodorizing material to be obtained decreases, and thus the photosensitizing colorants in the deodorizing material are not easily excited. This results in a difficulty in a production of singlet oxygen. As will be demonstrated in examples to be discussed later, according to the deodorizing material that was obtained by blending the photosensitizing colorants of 3.0 g to the unsaturated polyester resin composition of 100 ml, the light transmissivity became substantially zero, and only photosensitizing colorants directly irradiated with light or indirectly irradiated with reflected light are photo-excited. Hence, single oxygen cannot be produced efficiently, and thus the deodorizing effect is not excellent.

Instead of the unsaturated polyester resin composition, when a polyacrylic resin composition or a polyepoxy resin composition and the like that has a high transparency is applied, as will be demonstrated in examples to be discussed later, the deodorization performance was low although it had a light transmissivity. The reason is not certain, but this may be because when the photosensitizing colorants are dissolved in the polyacrylic resin composition or the polyepoxy resin composition and the like, the photosensitizing colorants are not completely dissolved in the polyacrylic resin composition, and the photosensitizing colorants are dispersed therein as fine particles as those are. Light that has collided with the photosensitizing colorants may be blocked by other photosensitizing colorants, causing an attenuation of light. Accordingly, some photosensitizing colorants are not excited, and thus singlet oxygen is not produced well.

The above-explained deodorizing material can be used at a location to which natural light or light from a light emitting device or the like is emitted, and through which air containing the odor components circulates. In addition, when the deodorizing material is applied in combination with a deodorizing device to be discussed later, the deodorization performance becomes further efficient.

(Deodorizing Device)

Next, an explanation will be given of a deodorizing device with reference to some examples. As illustrated in FIG. 1, a first example deodorizing device 1 includes a container 10, a light emitting device 40, an inlet 30, an outlet 20, and an air circulation device 50.

The container 10 is a space which has deodorizing materials 100 filled therein, and which is for decomposing the odor components contained in air flowing in this space.

The container 10 has a deodorizing material mount plate 11 placed so as to be apart from the bottom of the container 10. The deodorizing materials 100 are disposed on this deodorizing material mount plate 11. The deodorizing material mount plate 11 is formed with multiple ventilation holes 11a that have a smaller diameter than the outer diameter of the deodorizing material 100. An example deodorizing material mount plate 11 is a net which does not allow the mounted deodorizing materials 100 not to fall down, and which permits air to flow therethrough.

In addition, the container 10 is connected with the inlet 30 that guides air between the container 10 and the deodorizing material mount plate 11, and is also connected with the outlet 20 that discharges the air having the odor components decomposed to the exterior.

Still further, the light emitting device 40 that emits light to the deodorizing materials 100 is provided in the container 10. An example light emitting device 40 is an LED (Light Emitting Diode), an EL (Electro Luminescence), a cold-cathode tube, or the like which is a light source that can be placed in the container 10. In order to make the photosensitizing colorants photo-excited, a light source with a high light intensity is preferably applied, and it is preferable that the light source should have a light intensity of equal to or higher than 30,000 lx.

Yet still further, the container 10 is provided with the air circulation device 50 that discharges the air in the container to the exterior through the outlet 20. In this case, the term air circulation device 50 means at least a device which forcibly supplies air in the deodorizing device 1, and which allows that air to efficiently contact the deodorizing materials 100 filled in the deodorizing device 1, and, is a device which performs a forcible air circulation in the deodorizing device 1 as needed. In this case, a fan is applied as the air circulation device 50.

Next, an explanation will be given of a flow of the deodorizing operation by the deodorizing device 1. The flow of air is indicated by arrows expressed by dashed lines.

Upon actuation of the air circulation device 50, air is flown into the container 10 through the inlet 30. The flowing air passes through the ventilation holes 11a, and contacts the deodorizing materials 100. Since the deodorizing materials 100 are irradiated with light by the light emitting device 40, the photosensitizing colorants in the deodorizing materials 100 are excited, and become a singlet excitation state, and further a triplet excitation state from the base state. The photosensitizing colorants give the energy thereof to oxygen molecules in the base state, thereby producing singlet oxygen. This singlet oxygen contacts the odor components, and decomposes the odor components. The air having the odor components decomposed is discharged from the interior of the container 10 through the outlet 20.

The deodorizing materials 100 are light transmissive, and thus light passing through some deodorizing materials 100 can reach the remaining deodorizing materials 100 located backwardly (in the example in FIG. 1, the deodorizing materials 100 located at the downward side not directly facing the light emitting device 40). Hence, all deodorizing materials 100 are irradiated with light, and the photosensitizing colorants in all deodorizing materials 100 can be excited. Accordingly, singlet oxygen can be produced efficiently, resulting in an excellent decomposition performance.

Figure 2:
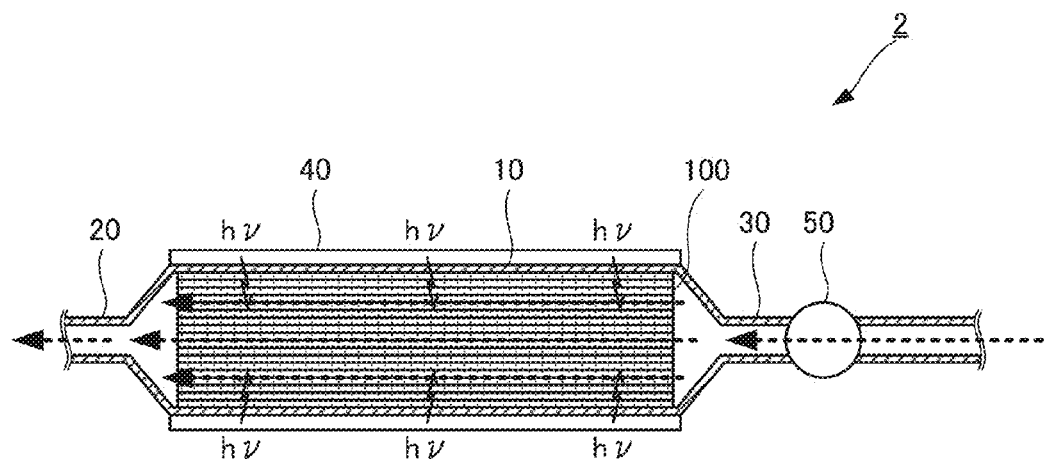
FIG. 2 is a schematic structural diagram illustrating a second example deodorizing device.

Next, an explanation will be given of a second example deodorizing device 2 with reference to FIG. 2.

The container 10 is in a cylindrical shape, and has the inlet 20 and the outlet 20 connected at both ends. In addition, the inlet 30 is provided with the air circulation device 50 which guides air into the container 10 and which discharges the air from the container 10 to the exterior through the outlet 20. A conventionally well-known device like a blower or a pump is applied as the air circulation device 50.

Multiple deodorizing materials 100 each in a bar shape having a circular cross section are disposed in the container 10.

The light emitting device 40 is disposed around the outer circumference of the container 10. According to a structure in which light is emitted to the deodorizing materials 100 in the container 10 from the exterior thereof, the container 10 is formed of a highly transparent material that has a high light transmissivity, and the light emitted by the light emitting device 40 can reach the deodorizing materials 100 through the container 10.

The other matters are the same as those of the first example deodorizing device 1. Hence, the explanation thereof will be omitted.

Next, an explanation will be given of a third example deodorizing device 3 with reference to FIG. 3. The deodorizing device 3 employs a so-called cyclone structure.

The container 10 includes a cylindrical outer cylinder 12 that has a lower part formed in a reversed conical shape, and an inner cylinder 13 located inwardly relative to the outer cylinder 12. The outer cylinder 12 and the inner cylinder 13 are disposed coaxially.

The inner cylinder 13 is provided with the air circulation device 50 that suctions air in the container 10 and discharges the suctioned air to the exterior, and the inner cylinder 13 functions as the outlet. In addition, the upper portion of the outer cylinder 12 is provided with the inlet 30 that guides air from the exterior in the tangential direction of the outer cylinder 12.

In addition, the multiple deodorizing materials 100 are filled in the outer cylinder 12. The outer cylinder 12 is formed of a light transmissive material, and the light emitting device 40 is provided so as to encircle the outer cylinder 12. Hence, light can be emitted to the deodorizing materials 100 filled in the container 10.

Figure 3A:
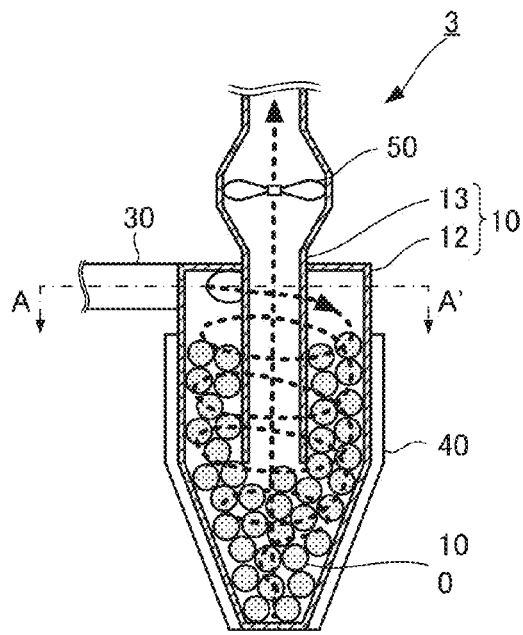
FIG. 3A is a schematic structural diagram illustrating a third example deodorizing device, and is a vertical cross-sectional view.
Figure 3B:
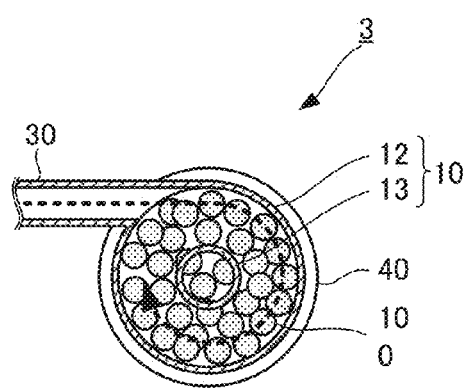
FIG. 3B is a schematic structural diagram illustrating the third example deodorizing device, and is a horizontal cross-sectional view in an A-A' direction in FIG. 3A.

Upon actuation of the air circulation device 50, as is indicated by arrows expressed by dashed lines in FIGS. 3A and 3B, air is guided in the container 10 through the inlet 30. The air guided in the space surrounded by the outer cylinder 12 and the inner cylinder 13 turns spirally, once goes downwardly, and then goes upwardly through the interior of the inner cylinder 13, and, eventually discharged to the exterior. Since the deodorizing materials 100 are filled in the container 10, upon irradiation with light, the photosensitizing colorants in the deodorizing materials 100 are excited, singlet oxygen is produced, and thus the odor components in the air are decomposed. Since the deodorizing materials 100 are light transmissive, light passing through some deodorizing materials 100 located at the external side in the container 10 (the deodorizing materials 100 located near the outer cylinder 12) can reach the remaining deodorizing materials 100 located at the internal side in the container 100 (the deodorizing materials 100 located near the inner cylinder 13). Hence, individual deodorizing materials 100 filled in the container can be irradiated with light, and the photosensitizing colorants in each deodorizing material 100 are excited. Accordingly, singlet oxygen can be produced efficiently.

The other matters are the same as those of the first example deodorizing device 1. Hence, the duplicated explanation thereof will be omitted.

Several specific examples of the deodorizing device are explained, but the form of the deodorizing device is not limited to the above-explained examples. Various forms are possible as long as such a form includes a container where the deodorizing materials can be disposed, the light emitting device that can emit light to the deodorizing materials in the container, the inlet that guides air in the container, the outlet that discharges the air to the exterior from the container, and the air circulation device that guides air in the chamber or discharges air from the container to the exterior.

In the above-explained examples, the explanation was given of the examples which employ the light emitting device 40, but in an environment where solar light or light from other lighting devices and the like can be emitted, the light emitting device 40 may be omitted.

The deodorizing material and the deodorizing device can be utilized in various applications, such as an indoor air conditioning device, a vehicular air conditioning device, and a refrigerator.

EXAMPLES

Deodorizing materials were prepared as follow, and the deodorization performance of the obtained deodorizing materials were examined.

(Preparation of Deodorizing Material)

Rose bengal of 1.5 g was added to unsaturated polyester resin composition (clear polyester resin (product number: F-04 made by EPOCH Corporation)) of 100 ml, the unsaturated polyester resin composition was stirred to dissolve the rose bengal therein.

Next, a curing agent (PERCURE-HB (product name, made by NOF Corporation) (compositions: ethyl-methyl-ketone-peroxide, and dimethyl phthalate)) of 2 ml was added, the solution was poured in a mold form, and was cured to obtain the deodorizing material.

The deodorizing material was taken out from the mold form, and was crushed in a shape mentioned in the following each test condition. This deodorizing material will be referred to as a deodorizing material Es1.5.

In addition, rose bengal of 2.0 g and of 3.0 g were respectively added to the clear polyester resin of 100 ml, and the deodorizing materials were obtained through the same procedures as explained above. Those deodorizing materials will be referred to as a deodorizing material Es2.0 and a deodorizing material Es3.0, respectively.

In addition, deodorizing materials were also prepared using a polyacrylic resin. Rose bengal of 1.0 g was added to an acrylic resin composition (acrylic resin SS101, made by EPOCH Corporation) (base resin: methyl methacrylate (66 wt %), and acrylic resin (34 wt %)) of 100 g, the resin composition was stirred, and a curing agent (NYPER-E (product name, made by NOF Corporation) (constituent: benzoyl-peroxide)) of 0.25 g was added thereto. Subsequently, a deodorizing material was obtained likewise the aforementioned cases. This deodorizing material will be referred to as a deodorizing material Ac1.0.

Still further, deodorizing materials were also obtained likewise the aforementioned cases except that the amount of added rose bengal was changed to 2.0 g and 3.0 g. Those deodorizing materials will be referred to as a deodorizing material Ac2.0, and a deodorizing material Ac3.0, respectively.

Yet still further, a deodorizing material was prepared using a polyepoxy resin. By applying an epoxy resin composition (highly transparent epoxy resin (PROCRYSTAL 770: base resin (epoxy resin obtained by polymerization of bisphenol A and epichlorohydrin)) of 200 g, and a curing agent (blended with denatured alicyclic polyamine and denatured alicyclic polyamine) of 130 g) (made by TEMCOFINE Co., Ltd.), a deodorizing material was obtained likewise the aforementioned cases except that rose bengal of 2 g was added. This deodorizing material will be referred to as a deodorizing material Ep.

Note that preparation of all of the above-explained deodorizing materials was carried out at a room temperature. Each of the obtained deodorizing materials was examined as follow.

First Example

Examination of Flow Rate of Mixture Gas Affecting Deodorization Performance

Figure 4:
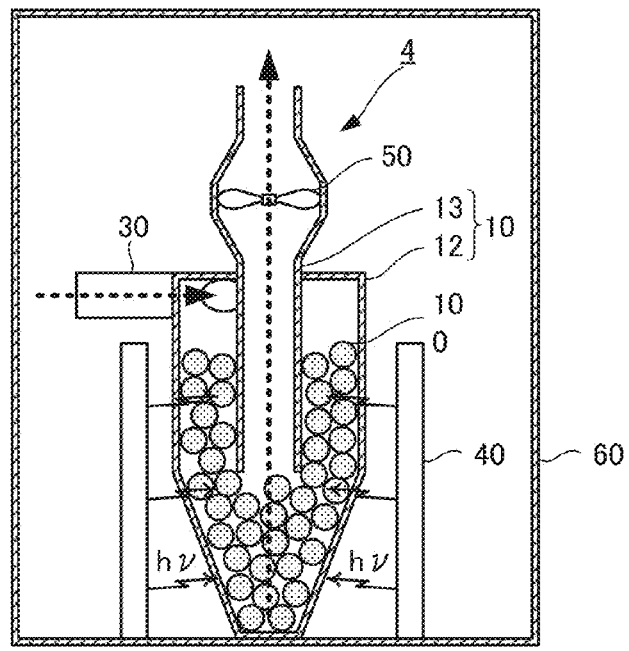
FIG. 4 is a schematic structural diagram illustrating a deodorizing device applied in an example.

FIG. 4 illustrates a device structure applied to examine the deodorization performance of the deodorizing material. The cyclone type deodorizing device 4 was prepared, and the deodorizing materials were filled in the container 10. Next, this deodorizing device 4 was placed in a chamber 60. The interior of the chamber 60 is a sealed dark room. The internal volume of the container 10 (a volume that can be filled with deodorizing materials) was 1 L, while the internal volume of the chamber 60 was 5 L.

A mixture gas of an odor gas and air was filled in the chamber 60, and the device was actuated. The mechanism was as follow: the mixture gas in the chamber 60 entered the container 10 through the inlet 30, contacted the deodorizing materials in the container 10, and discharged to the chamber 60 through the outlet, and thus the mixture gas was circulated through the interior of the container 10. Next, the remaining percentage of the odor gas in the chamber 60 was measured over time. In addition, the flow rate of the mixture gas was measured at the inlet of the deodorizing device 4.

The odor gas in the mixture gas was decomposed under the test conditions described below.

Figure 5:
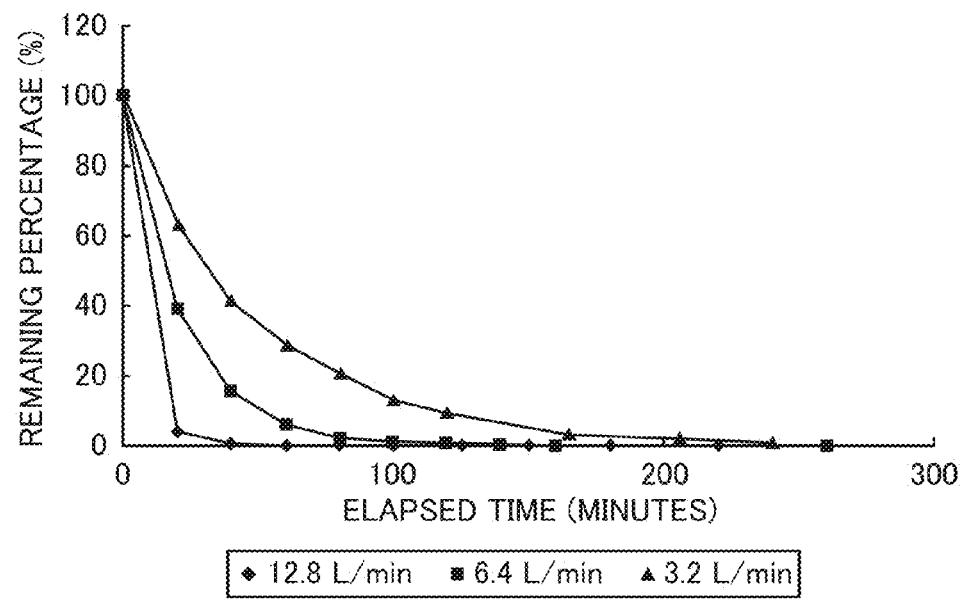
FIG. 5 is a graph illustrating a change with time in the remaining percentage of odor gas in a first example.

Light intensity: 30,000 lx
Filled deodorizing materials: deodorizing materials Es2.0 (in a substantially prismatic body shape of 3-10 mm)
Filled amount of deodorizing materials: 160 g
Odor gas: methyl-mercaptan
Flow rate of mixture gas: 12.8 L/min, 6.4 L/min, and 3.2 L/min FIG. 5 shows the test results. In any flow rates, the final remaining percentage of methyl-mercaptan became 0%, and it becomes clear that methyl-mercaptan was completely decomposed. In addition, the faster the flow rate of the circulating mixture gas was, the faster the decomposition speed of methyl-mercaptan became. This is because the number of contacts between singlet oxygen produced by the photosensitizing colorants and methyl-captane may increase when the flow rate of the mixture gas becomes fast.

Second Example

Examination of Flow Rate of Odor Gas Affecting Deodorization Performance

Figure 6:
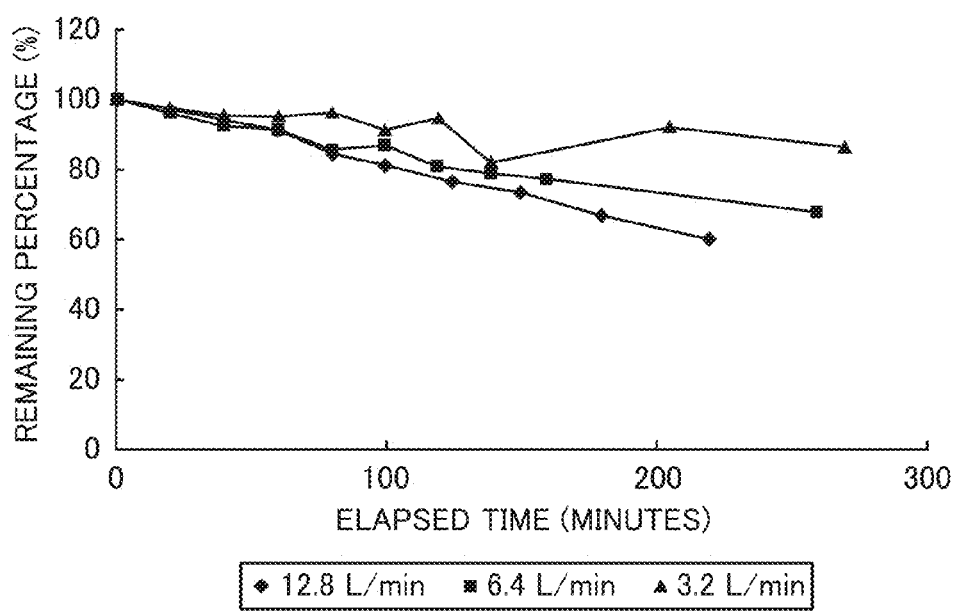
FIG. 6 is a graph illustrating a change with time in the remaining percentage of odor gas in a second example.

Next, a test was carried out like the first example except that the odor gas was changed to dimethyl sulfide.
The test conditions were as follows.
Light intensity: 30,000 lx
Filled deodorizing materials: deodorizing materials Es2.0 (in a substantially prismatic body shape of 3-10 mm)
Filled amount of deodorizing materials: 160 g
Odor gas: dimethyl sulfide
Flow rate of mixture gas: 12.8 L/min, 6.4 L/min, and 3.2 L/min FIG. 6 shows the test results. Although the decomposition speed was slow in comparison with that of methyl-mercaptan, the remaining percentage of dimethyl sulfide gradually decreased, and it is verified that dimethyl sulfide can be decomposed. In addition, like methyl-mercaptan, the faster the flow rate of the mixture gas was, the faster the decomposition speed became.

Third Example

Figure 7:
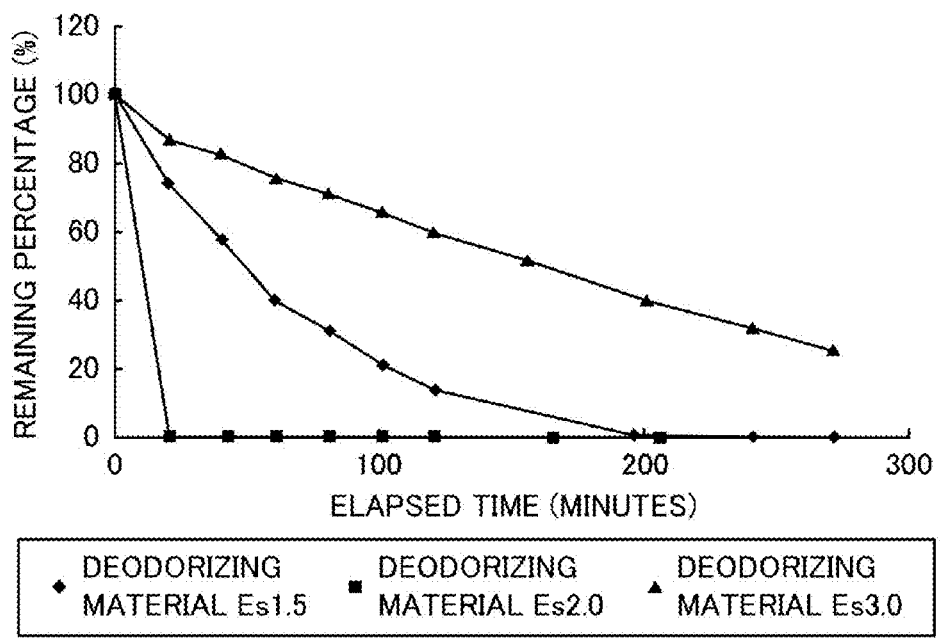
FIG. 7 is a graph illustrating a change with time in the remaining percentage of odor gas in a third example.

Examination of Action According to Blending Ratio Between Photosensitizing Colorants and Unsaturated Polyester Resin Composition Next, how the blending ratio of the photosensitizing colorants in an unsaturated polyester resin composition affects the decomposition of odor gas was examined.
Like the first example, methyl-mercaptan was decomposed under the following test conditions.
Light intensity: 30,000 lx
Filled deodorizing materials: deodorizing materials Es1.5, deodorizing materials Es2.0, and deodorizing materials Es3.0 (all in a substantially prismatic body shape of 3-10 mm)
Filled amount of deodorizing materials: 160 g
Odor gas: methyl-mercaptan
Flow rate of mixture gas: 12.8 L/min FIG. 7 illustrates the test results. The deodorizing material Es2.0 had the fastest decomposition speed, and after 20 minutes had elapsed, the remaining percentage of methyl-mercaptan became 0%. In the case of the deodorizing material Es1.5, the remaining percentage of methyl-mercaptan after 20 minutes had elapsed became 0%. Conversely, the deodorizing material Es3.0 had the slow decomposition speed, and even 20 minutes had elapsed, methyl-mercaptan remained. This is because, according to the deodorizing material Es3.0, only the photosensitizing colorants in the deodorizing materials located at the external side of the chamber (a side irradiated with light) were excited since the light transmissivity was substantially 0% as will be discussed later, and the amount of produced singled oxygen was little.

Fourth Example

Figure 8:
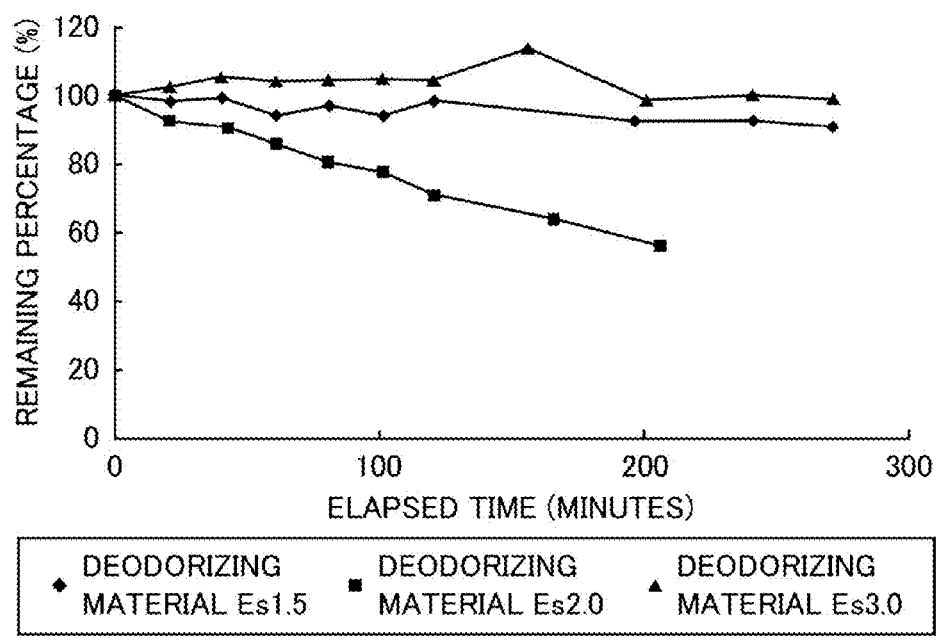
FIG. 8 is a graph illustrating a change with time in the remaining percentage of odor gas in a fourth example.

Examination of Action of Blending Ratio Between Photosensitizing Colorants and Unsaturated Polyester Resin Composition Affecting Decomposition Performance Next, a test was carried out like the third example except that the odor gas was changed to dimethyl sulfide.
The test conditions were as follows:
Light intensity: 30,000 lx
Filled deodorizing materials: deodorizing materials Es1.5, deodorizing materials Es2.0, and deodorizing materials Es3.0 (all in a substantially prismatic body shape of 3-10 mm)
Filled amount of deodorizing materials: 160 g
Odor gas: dimethyl sulfide
Flow rate of mixture gas: 12.8 L/min FIG. 8 shows the test results. Comprehensively, the decomposition speed was slow in comparison with that of methyl-mercaptan, but like the third example, there was a tendency that the decomposition speed became faster in the order of the deodorizing materials Es2.0, the deodorizing materials Es1.5, and the deodorizing materials Es3.0.

First Comparative Example

Examination of Decomposition Performance of Deodorizing Material Ac

Figure 9:
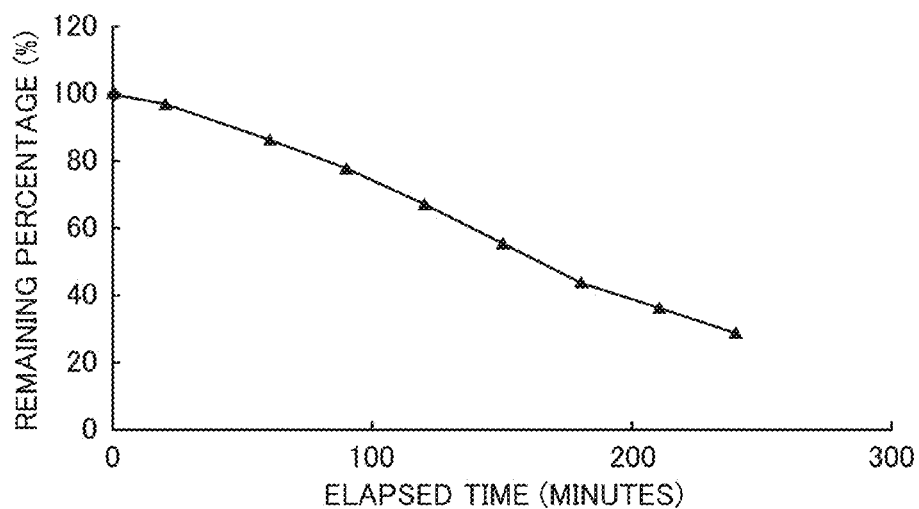
FIG. 9 is a graph illustrating a change with time in the remaining percentage of odor gas in a first comparative example.

Next, a test was carried out for the decomposition performance of the deodorizing materials Ac prepared using a polyacrylic resin composition instead of the unsaturated polyester resin composition.
Light intensity: 30,000 lx
Filled deodorizing materials: deodorizing materials Ac2.0 (in a substantially prismatic body shape of 3-10 mm)
Filled amount of deodorizing materials: 160 g
Odor gas: methyl-mercaptan
Flow rate of mixture gas: 12.8 L/min FIG. 9 shows the test results. In the case of the deodorizing material Es2.0, the remaining percentage of methyl-mercaptan was 2-3% after 20 minutes had elapsed, and thus the odor gas was substantially completely decomposed. Conversely, in the case of the deodorizing material Ac2.0, the remaining percentage of methyl-mercaptan was 90-95%, and thus the odor gas was hardly decomposed. That is, it becomes clear that in the case of the deodorizing material Ac2.0, the decomposition speed of methyl-mercaptan was quite slow in comparison with the deodorizing material Es2.0 having the same blending amount of rose bengal. This is because even if the deodorizing material Ac2.0 was irradiated with light, the rose bengal in the deodorizing material Ac2.0 was hardly photo-exited, and thus the amount of produced singlet oxygen may be little. In view of foregoing, the deodorizing material obtained using an acrylic resin composition has a poor deodorization effect, and is not suitable as the deodorizing material.

First Examination Example

Examination of Light Transmissivity and Absorbance Spectrum

With regard to a difference in the decomposition performance of the odor components between the polyacrylic resin composition and the unsaturated polyester resin composition, in order to further proceed the tests, the transmission factor of the deodorizing materials Es and that of the deodorizing materials Ac were measured.

Respective deodorizing materials Es1.5, 2.0, and 3.0 (thickness: 2 mm, width: 8 mm, and length: 20 mm) were inserted in a cell of a HITACHI spectral photometer (U-2001), and absorbancy up to the wavelength of 700 nm to 400 nm was scanned. Next, the absorbancy at the maximum absorption wavelength of rose bengal that is 567 nm was measured, thereby obtaining the transmission factor.

When six sheets of paper blackened with a marker and laminated one another were filled in a cell, and the absorbancy was measured while blocking light, the absorbancy was close to 2. Hence, this absorbancy was set as 0% of transmission factor, and respective transmission factors were obtained through a conversion.

Table 1 shows absorbancy and transmission factor of each deodorizing material Es1.5, 2.0, and 3.0. A polyester resin in table 1 was obtained without adding rose bengal through the preparation of the above-explained deodorizing materials Es.

TABLE 1

| Polyester Resin | | Deodorizing Material Es1.5 | | Deodorizing Material Es2.0 | | Deodorizing Material Es3.0 | |
| --- | --- | --- | --- | --- | --- | --- | --- |
| Absorbancy | Transmission Factor (%) | Absorbancy | Transmission Factor (%) | Absorbancy | Transmission Factor (%) | Absorbancy | Transmission Factor (%) |
| 0.16 | 91.8 | 1.25 | 38.1 | 1.87 | 7.2 | 2.01 | 0.0 |

As is clear from table 1, in the cases of the deodorizing materials (deodorizing materials Es1.5, 2.0, and 3.0) obtained using the unsaturated polyester resin composition, when the blending amount of colorants increased, the transmission factor decreased. It becomes clear that in the case of the deodorizing material Es3.0, the transmission factor was 0%, and thus substantially no light passed through it. This may be a reason that the decomposition speed of methyl-captane and dimethyl sulfide by the deodorizing material Es3.0 in the third and fourth examples was slow.

Likewise, the absorbancy of each deodorizing material Ac1.0, 2.0, and 3.0 (thickness: 1 mm, width: 8 mm, and length: 20 mm) was measured, and the transmission factor was obtained. Each kind of the deodorizing materials Ac1.0, 2.0, and 3.0 was double-layered to accomplish a thickness of 2 mm, and then the absorbancy was measured. The absorbancy and transmission factor of each deodorizing material Es1.5, 2.0, and 3.0 are shown in table 2.

TABLE 2

| Deodorizing Material Ac1.0 | | Deodorizing Material Ac2.0 | | Deodorizing Material Ac3.0 | |
| --- | --- | --- | --- | --- | --- |
| Absorbancy | Transmission Factor (%) | Absorbancy | Transmission Factor (%) | Absorbancy | Transmission Factor |
| 1.56 | 21.5 | 1.53 | 22.6 | 1.98 | 0.0 |

As is clear from table 2, in the cases of the deodorizing materials Ac1.0 and the deodorizing material Ac2.0 obtained using the polyacrylic resin composition, even if the blending amount of colorants changed, there was no substantial change in transmission factor, and in the case of the deodorizing material Ac3.0, the transmission factor was 0%.

Figure 10:
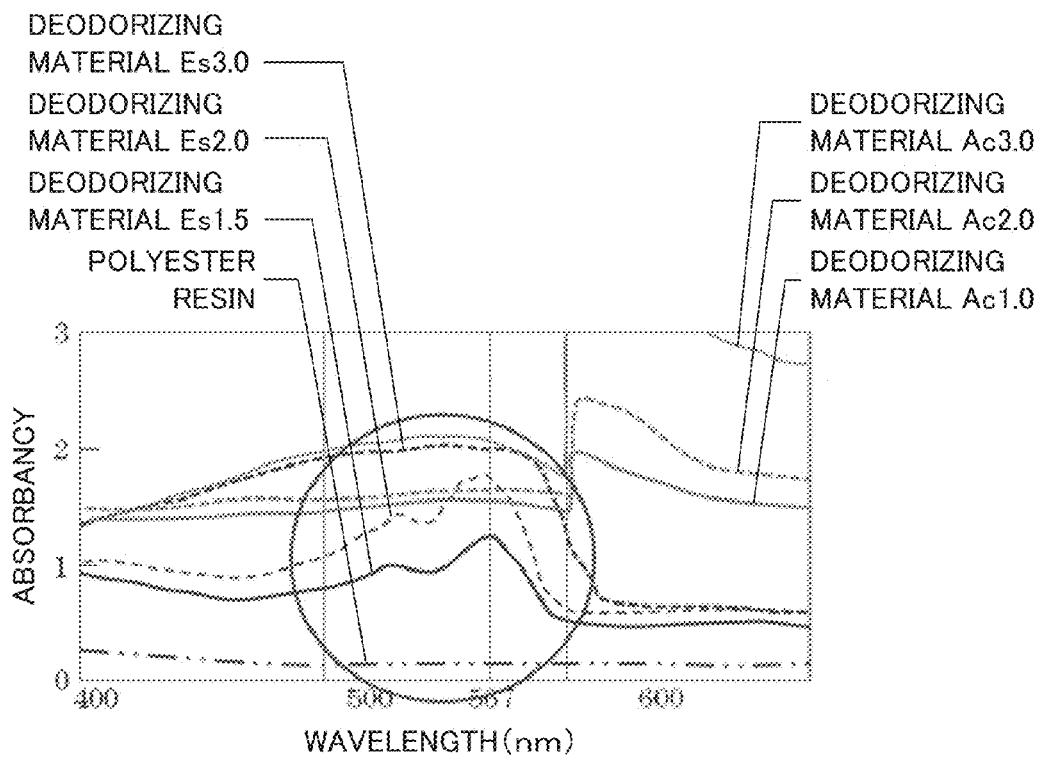
FIG. 10 is a diagram illustrating absorbance spectra of a deodorizing material Es and a deodorizing material Ac.

In addition, the absorbance spectra of the deodorizing materials Es1.5, 2.0, and 3.0, the deodorizing materials Ac1.0, 2.0, and 3.0, and the polyester resin are shown in FIG. 10 for examination.

In the cases of the deodorizing materials Es1.5 and 2.0, the unique peak to rose bengal can be seen within a range from 500 nm to 600 nm (a circled portion in FIG. 10). That is, it is shown that rose bengal in the deodorizing materials Es1.5 and 2.0 are excited and singlet oxygen can be produced. In the case of the deodorizing material Es3.0, since the transmission factor was 0%, the similar peak cannot be seen.

Conversely, in the cases of the deodorizing materials Ac1.0 and 2.0, although the transmission factor was equal to or higher than 20%, none of such deodorizing materials show the unique peak to rose bengal that can be seen in the deodorizing materials Es1.5 and 2.0. This indicates that even if rose bengal is dispersed in the acrylic resin, no rose bengal is photo-excited, that is, no singlet oxygen can be produced, resulting in the lack of the decomposition mechanism of odor components by the production of singlet oxygen.

Second Examination Example

Examination of Solubility of Photosensitizing Colorant to Resin Composition

A beaker filled with 200 ml of water was prepared, and the deodorizing material Es2.0 (10 g in a substantially prismatic body shape of 3-10 mm) was put therein. Likewise, the deodorizing material Ac2.0 (10 g in a substantially prismatic body shape of 3-10 mm), and the deodorizing material Ep (10 g in a substantially prismatic body shape of 3-10 mm) were respectively put in water.

In the cases of the deodorizing materials Ac2.0 and the deodorizing material Ep, water was immediately colored with a red color right after such deodorizing materials were put in the water. It becomes clear that in the cases of the deodorizing materials Ac2.0 and the deodorizing material Ep, rose bengal in the resin are soluble. This shows that the particles of rose bengal are not fully dissolved in the acrylic resin and the epoxy resin, and are in a condition in which such particles are simply dispersed in the resin.

Conversely, in the case of the deodorizing material Es2.0, even if the deodorizing material was put in water and left as it was for over three minutes, the water was hardly colored. This shows that since the solubility between the unsaturated polyester resin and rose bengal was excellent, and the rose bengal was well dissolved in the unsaturated polyester resin, and thus the rose bengal was not solved in the water.

In view of foregoing results, it becomes clear that the deodorizing material which has a function of producing singlet oxygen by photo-excitation of photosensitizing colorants and of decomposing odor components cannot be obtained depending on the kind of resin composition in which the photosensitizing colorants are dissolved, but when the unsaturated polyester resin composition and the photosensitizing colorants are combined, the photosensitizing colorants can be well dissolved, and the deodorizing material which has an excellent deodorization performance can be obtained.

The present disclosure permits various embodiments and modifications thereof without departing from the scope of the present disclosure. The embodiments described above are to explain the present disclosure, and are not intended to limit the scope of the present disclosure.

This application claims the priority based on Japanese Patent Application No. 2012-178967 filed on Aug. 10, 2012. The whole specification, claims and drawings of Japanese Patent Application No. 2012-178967 are herein incorporated in this specification by reference.

INDUSTRIAL APPLICABILITY

As explained above, the deodorizing material of the present disclosure is a cured substance obtained by dissolving the photosensitizing colorants in the unsaturated polyester resin composition which contains unsaturated polyester and a monomer that can be copolymerized with the unsaturated polyester, and which is in a liquid state at a room temperature, and by adding the curing agent to let the liquid cured. Since it is a solid body that can be formed in a desired size, the handling of the deodorizing material is easy and the deodorizing material can be built in various deodorizing devices. Hence, the general versatility is excellent. In addition, since the deodorizing material is light transmissive, emitted light passes through the deodorizing material, and can reach other deodorizing materials that do not directly face with a light source. Since the photosensitizing colorants in the deodorizing materials not directly facing with the light source are also excited, singlet oxygen can be efficiently produced, resulting in an excellent decomposition performance of odor components. Therefore, the deodorizing material can be applied to various devices, such as an indoor air conditioning device, a vehicular air conditioning device, and a refrigerator.

REFERENCE SIGNS LIST

1 Deodorizing device
2 Deodorizing device
3 Deodorizing device
4 Deodorizing device
10 Container
11 Deodorizing material mount plate
11a Ventilation hole
12 Outer cylinder
13 Inner cylinder
20 Outlet (outlet channel)
30 Inlet (Inlet channel)
40 Light emitting device
50 Air circulation device
60 Chamber
100 Deodorizing material

What is claimed is:

1. A deodorizing material comprising:
a rose bengal dissolved in an unsaturated polyester resin composition containing an unsaturated polyester and a monomer copolymerizable with the unsaturated polyester in a liquid state at room temperature to form a cured substance by the addition of a curing agent
wherein the rose bengal is excited upon irradiation with light in a gas phase containing oxygen and an odor component, to produce singlet oxygen, thereby decomposing the odor component.

2. The deodorizing material according to claim 1, wherein the rose bengal is equal or greater than 1.5 g and less than 3.0 g in 100 ml of the unsaturated polyester resin composition.

3. A deodorizing device comprising:
a container in which the deodorizing material according to claim 2 is filled;
an inlet that guides air containing an odor component into the container; and
an outlet that discharges the air from the container.

4. The deodorizing device according to claim 3, further comprising an air circulation device that causes, through the inlet and the outlet, the air to be in contact with each deodorizing material filled in the container.

5. The deodorizing device according to claim 3, further comprising a light emitting device that emits light to the deodorizing material.

6. The deodorizing device according to claim 4, further comprising a light emitting device that emits light to the deodorizing material.

7. A deodorizing material producing method comprising:
dissolving a rose bengal in an unsaturated polyester resin composition which contains unsaturated polyester and a monomer copolymerizable with the unsaturated polyester, in a liquid state at room temperature with addition of a curing agent to let the liquid cure.

8. The deodorizing material producing method according to claim 7, wherein the rose bengal is of equal to or greater than 1.5 g and less than 3.0 g in 100 ml of the unsaturated polyester resin composition.

9. A deodorizing device comprising:
a container, filled with a deodorizing material, the deodorizing material being composed of a rose bengal dissolved in an unsaturated polyester resin composition containing an unsaturated polyester and a monomer copolymerizable with the unsaturated polyester in a liquid state at room temperature to form a cured substance by the addition of a curing agent, wherein the rose bengal is excited upon irradiation with light in a gas phase containing oxygen and an odor component to produce singlet oxygen, thereby decomposing the odor component
an inlet that guides air containing an odor component into the container; and
an outlet that discharges the air from the container.

10. The deodorizing device according to claim 9, further comprising an air circulation device that causes, through the inlet and the outlet, the air to be in contact with each deodorizing material filled in the container.

11. The deodorizing device according to claim 9, further comprising a light emitting device that emits light to the deodorizing material.

12. The deodorizing device according to claim 10, further comprising a light emitting device that emits light to the deodorizing material.

* * * * *